United States Patent
Cunningham et al.

(10) Patent No.: US 11,364,068 B2
(45) Date of Patent: Jun. 21, 2022

(54) SPLIT ELECTRODE FOR USE IN A BIPOLAR ELECTROSURGICAL INSTRUMENT

(71) Applicant: COVIDIEN LP, Mansfield, MA (US)

(72) Inventors: James S. Cunningham, Boulder, CO (US); Paul R. Romero, Loveland, CO (US)

(73) Assignee: Covidien LP, Mansfield, MA (US)

( * ) Notice: Subject to any disclaimer, the term of this patent is extended or adjusted under 35 U.S.C. 154(b) by 1106 days.

(21) Appl. No.: 15/951,605

(22) Filed: Apr. 12, 2018

(65) Prior Publication Data
US 2018/0228531 A1   Aug. 16, 2018

Related U.S. Application Data

(63) Continuation of application No. 14/319,869, filed on Jun. 30, 2014, now Pat. No. 9,943,357.
(Continued)

(51) Int. Cl.
*A61B 18/14* (2006.01)
*A61B 18/00* (2006.01)

(52) U.S. Cl.
CPC ........... *A61B 18/1445* (2013.01); *A61B 2018/00083* (2013.01); *A61B 2018/00607* (2013.01);
(Continued)

(58) Field of Classification Search
CPC ............ A61B 18/1442; A61B 18/1445; A61B 18/145; A61B 2018/145; A61B 2018/1452; A61B 2018/1455; A61B 2018/1457
See application file for complete search history.

(56) References Cited

U.S. PATENT DOCUMENTS

D249,549 S    9/1978  Pike
4,200,104 A   4/1980  Harris
(Continued)

FOREIGN PATENT DOCUMENTS

CN    201299462 Y    9/2009
DE    2415263 A1    10/1975
(Continued)

OTHER PUBLICATIONS

U.S. Appl. No. 13/731,674, filed Dec. 31, 2012; inventor: Siebrecht.
(Continued)

*Primary Examiner* — Eun Hwa Kim

(57) ABSTRACT

An end-effector assembly includes opposing first and second jaw members, at least one of which is movable relative to the other from a first position wherein the jaw members are disposed in spaced relation relative to one another to at least a second position closer to one another wherein the jaw members cooperate to grasp tissue therebetween. Each jaw member includes an electrically-conductive, tissue-engaging structure extending along a length thereof. Each electrically-conductive, tissue-engaging structure is configured to connect to a source of electrosurgical energy for conducting electrosurgical energy through tissue grasped between the opposing first and second jaw members to effect a tissue seal. The end-effector assembly includes a split electrode including a first electrode portion and a second electrode portion spaced apart from the first electrode portion and electrically-isolated therefrom by a gap defined therebetween. The first and second electrode portions are associated with one of the electrically-conductive tissue-engaging structures.

14 Claims, 9 Drawing Sheets

Related U.S. Application Data

(60) Provisional application No. 61/878,468, filed on Sep. 16, 2013.

(52) U.S. Cl.
CPC ............ *A61B 2018/1455* (2013.01); *A61B 2018/1467* (2013.01)

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| D402,028 S | 12/1998 | Grimm et al. | |
| D408,018 S | 4/1999 | McNaughton | |
| 5,893,863 A * | 4/1999 | Yoon | A61B 18/1442 606/170 |
| D416,089 S | 11/1999 | Barton et al. | |
| D424,694 S | 5/2000 | Tetzlaff et al. | |
| D425,201 S | 5/2000 | Tetzlaff et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S * | 11/2010 | Kingsley | D24/144 |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,943,357 B2 | 4/2018 | Cunningham et al. | |
| 2005/0113827 A1* | 5/2005 | Dumbauld | A61B 18/1445 606/45 |
| 2005/0283148 A1 | 12/2005 | Janssen et al. | |
| 2007/0078456 A1* | 4/2007 | Dumbauld | A61B 18/1445 606/42 |
| 2007/0078458 A1 | 4/2007 | Dumbauld et al. | |
| 2008/0287948 A1 | 11/2008 | Newton et al. | |
| 2011/0028964 A1 | 2/2011 | Edwards | |
| 2012/0059371 A1* | 3/2012 | Anderson | A61B 18/085 606/45 |
| 2012/0095456 A1 | 4/2012 | Schechter et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009318 U1 | 8/2007 |
| DE | 202007009317 U1 | 10/2007 |
| DE | 202007016233 U1 | 1/2008 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 6502328 | 3/1992 |
| JP | 55106 | 1/1993 |
| JP | 0540112 | 2/1993 |
| JP | 6121797 | 5/1994 |
| JP | 6285078 | 10/1994 |
| JP | 06343644 A | 12/1994 |
| JP | 6511401 | 12/1994 |
| JP | 07265328 A | 10/1995 |
| JP | 856955 | 3/1996 |
| JP | 08252263 A | 10/1996 |
| JP | 8289895 | 11/1996 |
| JP | 8317934 | 12/1996 |
| JP | 8317936 | 12/1996 |
| JP | 910223 | 1/1997 |
| JP | 09000538 A | 1/1997 |
| JP | 9122138 | 5/1997 |
| JP | 1024051 | 1/1998 |
| JP | 0010000195 A | 1/1998 |
| JP | 10155798 | 6/1998 |
| JP | 1147149 | 2/1999 |
| JP | 1147150 | 2/1999 |
| JP | 11070124 | 3/1999 |
| JP | 11169381 | 6/1999 |
| JP | 11192238 | 7/1999 |
| JP | 11244298 A | 9/1999 |
| JP | 2000102545 A | 4/2000 |
| JP | 2000135222 A | 5/2000 |
| JP | 2000342599 A | 12/2000 |
| JP | 2000350732 A2 | 12/2000 |
| JP | 2001003400 A | 1/2001 |
| JP | 2001008944 | 1/2001 |
| JP | 2001029355 | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |

(56) References Cited

FOREIGN PATENT DOCUMENTS

| | | |
|---|---|---|
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 0006030945 B2 | 11/2016 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview", Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties At VHF Through Microwave Frequencies", IEEE Transactions on Microwave Theory and Techniques vol. MTT-28, No. 4, Apr. 1980 pp. 414-427.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer"; Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.

(56) References Cited

OTHER PUBLICATIONS

Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy"; FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005 LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed 12117/2008; inventor: Paul R. Sremeich.
US-H1745 dated Aug. 1, 1988 to Paraschac.
US-H1904, dated Oct. 3, 2000 to Yates et al.
US-H2037, dated Jul. 2, 2002 to Yates et al.

\* cited by examiner

SPLIT ELECTRODE FOR USE IN A BIPOLAR ELECTROSURGICAL INSTRUMENT

CROSS REFERENCE TO RELATED APPLICATION

The present application is a continuation application of U.S. patent application Ser. No. 14/319,869, filed on Jun. 30, 2014, which claims the benefit of and priority to U.S. Provisional Application Ser. No. 61/878,468, filed on Sep. 16, 2013, the entire contents of each of which are incorporated herein by reference.

BACKGROUND

1. Technical Field

The present disclosure relates to electrosurgical instruments. More particularly, the present disclosure relates to a bipolar electrosurgical instrument, such as, for example, a vessel-sealing device, including a jaw member that includes a split electrode adapted for tissue dissection and coagulation.

2. Discussion of Related Art

Electrosurgical instruments have become widely used by surgeons. Electrosurgery involves the application of electrical energy and/or electromagnetic energy to cut, dissect, ablate, coagulate, cauterize, seal or otherwise treat biological tissue during a surgical procedure. Electrosurgery is typically performed using an electrosurgical generator operable to output energy and a handpiece including a surgical instrument (e.g., end effector) adapted to transmit energy to a tissue site during electrosurgical procedures. Electrosurgery can be performed using either a monopolar or a bipolar instrument.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue. In monopolar electrosurgery, a patient return electrode, also called a grounding pad, bovie pad, neutral electrode or patient plate, is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode. In bipolar electrosurgery, both the active electrode and return electrode functions are performed at the site of surgery. Bipolar electrosurgical devices include two electrodes of opposite polarity that are located in proximity to one another for the application of current between their surfaces. Bipolar electrosurgical current travels from one electrode, through the intervening tissue to the other electrode to complete the electrical circuit, thereby eliminating the need for a remotely-located current return. Bipolar instruments generally include end-effectors, such as grippers, cutters, forceps, dissectors and the like.

Forceps utilize mechanical action to constrict, grasp, dissect and/or clamp tissue. By utilizing an electrosurgical forceps, a surgeon can utilize both mechanical clamping action and electrosurgical energy to effect hemostasis by heating the tissue and blood vessels to cauterize, coagulate/desiccate, seal and/or divide tissue. Bipolar electrosurgical forceps utilize two generally opposing electrodes that are operably associated with the inner opposing surfaces of an end effector and that are both electrically coupled to an electrosurgical generator. In bipolar forceps, the end-effector assembly generally includes opposing jaw members, at least one jaw member is pivotably mounted with respect to one another. In bipolar configuration, only the tissue grasped between the jaw members is included in the electrical circuit. By utilizing an electrosurgical forceps, a surgeon can cauterize, coagulate/desiccate and/or seal tissue and/or simply reduce or slow bleeding by controlling the intensity, frequency and duration of the electrosurgical energy applied through the jaw members to the tissue. During the sealing process, mechanical factors such as the pressure applied between opposing jaw members and the gap distance between the electrically-conductive tissue-contacting surfaces (electrodes) of the jaw members play a role in determining the resulting thickness of the sealed tissue and effectiveness of the seal.

A variety of types of end-effector assemblies have been employed for various types of electrosurgery using a variety of types of monopolar and bipolar electrosurgical instruments.

SUMMARY

A continuing need exists for a reliable electrosurgical instrument that includes an end-effector assembly including an electrode adapted for tissue dissection and coagulation.

According to an aspect of the present disclosure, an end-effector assembly is provided. The end-effector assembly includes opposing first and second jaw members, at least one of which is movable relative to the other from a first position wherein the jaw members are disposed in spaced relation relative to one another to at least a second position closer to one another wherein the jaw members cooperate to grasp tissue therebetween. Each jaw member includes an electrically-conductive, tissue-engaging structure extending along a length thereof. Each electrically-conductive, tissue-engaging structure is configured to connect to a source of electrosurgical energy for conducting electrosurgical energy through tissue grasped between the opposing first and second jaw members to effect a tissue seal. The end-effector assembly includes a split electrode including a first electrode portion and a second electrode portion spaced apart from the first electrode portion and electrically-isolated therefrom by a gap defined therebetween. The first and second electrode portions are associated with one of the electrically-conductive tissue-engaging structures. The split electrode is electrically-isolated from the first and second jaw members.

According to an aspect of the present disclosure, an electrosurgical system is provided. The electrosurgical system includes a source of electrosurgical energy and an electrosurgical instrument. The electrosurgical instrument includes a housing having a shaft affixed thereto. The shaft includes first and second jaw members attached to a distal end thereof, at least one of which movable relative to the other from a first position wherein the jaw members are disposed in spaced relation relative to one another to at least a second position closer to one another wherein the jaw members cooperate to grasp tissue therebetween. The electrosurgical instrument includes a first electrically-conductive, tissue-engaging structure extending along a length of the first jaw member and a second electrically-conductive, tissue-engaging structure extending along a length of the second jaw member. The first and second electrically-conductive, tissue-engaging structures are configured to connect to the source of electrosurgical energy for conducting electrosurgical energy through tissue grasped therebetween to effect a tissue seal. The electrosurgical instrument also includes a split electrode disposed in association with the first electrically-conductive, tissue-engaging structure. The split electrode includes a first electrode portion and a second electrode portion spaced apart from the first electrode portion and electrically-isolated therefrom by a gap defined therebetween.

BRIEF DESCRIPTION OF THE DRAWINGS

Objects and features of the presently-disclosed split electrode adapted for tissue dissection and coagulation, and electrosurgical instruments including the same, will become apparent to those of ordinary skill in the art when descriptions of various embodiments thereof are read with reference to the accompanying drawings, of which.

DETAILED DESCRIPTION

Figure 1:
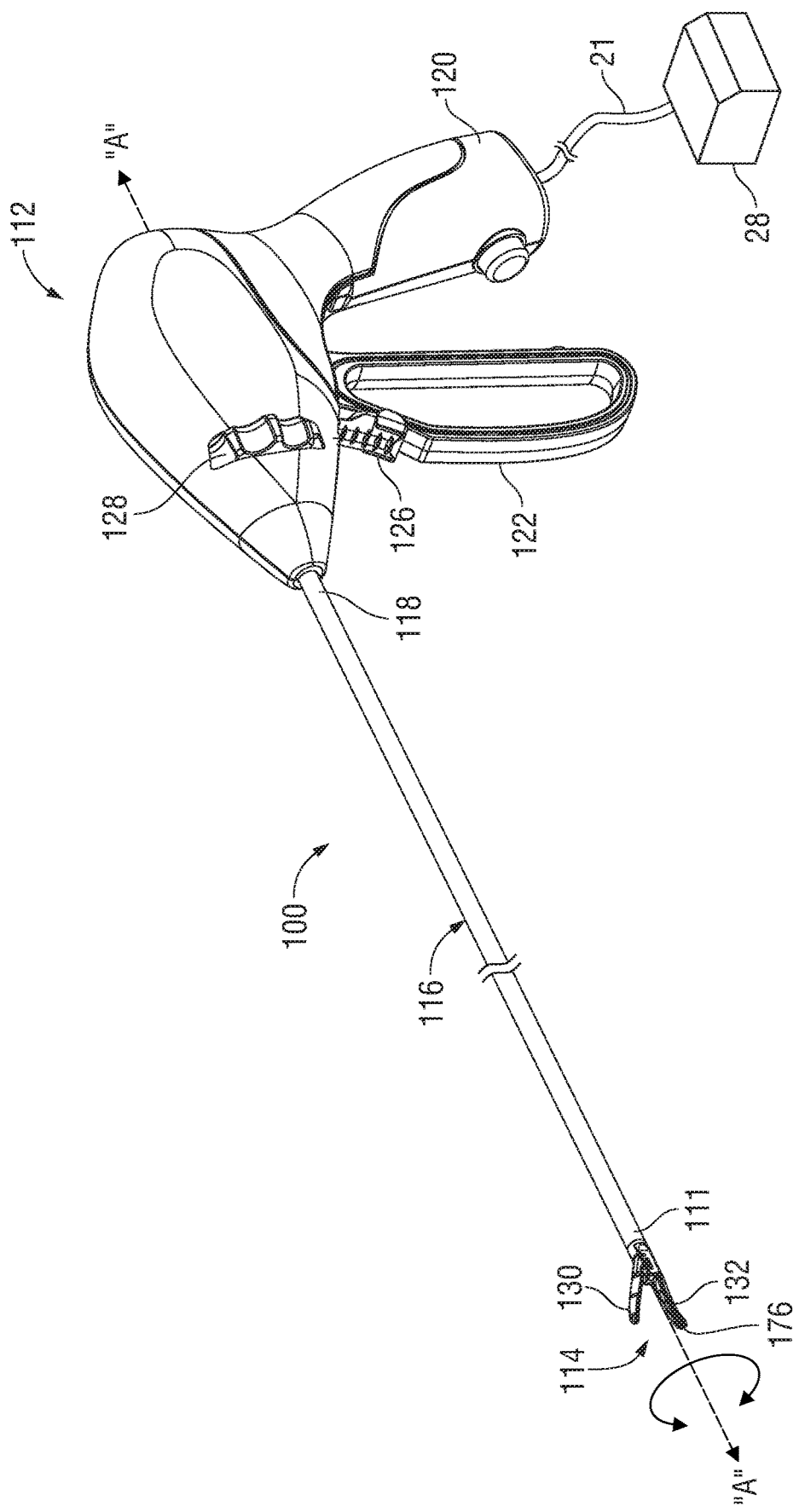
FIG. 1 is a perspective view of an electrosurgical forceps according to an embodiment of the present disclosure showing a housing, an elongated shaft, and an end-effector assembly.

Hereinafter, embodiments of a split electrode adapted for tissue dissection and coagulation of the present disclosure for use in bipolar electrosurgical instruments, and electrosurgical systems including the same, are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide electrosurgical instruments suitable for sealing, cauterizing, coagulating/desiccating, cutting and/or dissecting vessels and vascular tissue. Various embodiments of the present disclosure provide an electrosurgical forceps with an end-effector assembly including two jaw members disposed in opposing relation relative to one another. Various embodiments of the presently-disclosed jaw members include a split electrode adapted for tissue dissection and coagulation. Embodiments of the presently-disclosed end-effector assemblies may include jaw members arranged in a unilateral or bilateral configuration.

Various embodiments of the present disclosure provide a split electrode for use in bipolar electrosurgical instruments. Embodiments may be suitable for utilization in open surgical applications. Embodiments of the presently-disclosed electrosurgical instruments may be connected through a suitable bipolar cable to a generator and/or other suitable power source. Embodiments may be suitable for utilization with endoscopic and laparoscopic surgical procedures. Embodiments may be implemented using electrosurgical energy at RF frequencies or at other frequencies. Although the following description describes the use of an endoscopic bipolar forceps, the teachings of the present disclosure may also apply to a variety of electrosurgical devices that include jaw members.

Embodiments of the presently-disclosed split electrode may include a first electrode portion and a second electrode portion spaced apart from the first electrode portion and electrically-isolated therefrom by a gap defined therebetween and/or by an insulator disposed within the gap. In some embodiments, a portion of a split electrode of the present disclosure (e.g., split electrode 176 shown in FIGS. 1-3, split electrode 476 shown in FIGS. 4 and 5, split electrode 976 shown in FIGS. 9 and 10, and split electrode 1376 shown in FIGS. 11 and 12) extends distally from a distal-most end of a jaw member. In some embodiments, a portion of a split electrode of the present disclosure (e.g., split electrode 776 shown in FIGS. 7 and 8) extends outwardly from a lateral side of a jaw member. Embodiments of the presently-disclosed electrosurgical instrument including an end-effector assembly, and electrosurgical systems including the same, may include any feature or combination of features of the split electrode embodiments disclosed herein.

The various embodiments disclosed herein may also be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

In FIG. 1, an embodiment of an electrosurgical forceps 100 is shown for use with various surgical procedures and generally includes a housing 112, a stationary handle 120, a movable handle 122, a rotation knob 128, a trigger 126, and an end-effector assembly 114. End-effector assembly 114 generally includes two jaw members 130 and 132 disposed in opposing relation relative to one another. End-effector assembly 114 may include any of the split electrode embodiments disclosed herein. An embodiment of the end-effector assembly 114 that includes a split electrode 176 adapted for tissue dissection and coagulation is shown in more detail in FIGS. 2A and 3. It is to be understood, however, that other end-effector assembly embodiments may also be used.

One or more components of the electrosurgical forceps 100, e.g., the housing 112, the stationary handle 120, the movable handle 122, the rotation knob 128, the trigger 126, and/or the end-effector assembly 114 may be adapted to mutually cooperate to grasp, seal and/or divide tissue, e.g., tubular vessels and vascular tissue (not shown). As depicted in FIG. 1, the end-effector assembly 114 is rotatable about a longitudinal axis "A-A" through rotation, either manually or otherwise, of the rotation knob 128. Forceps 100 may include additional, fewer, or different components than shown in FIG. 1, depending upon a particular purpose or to achieve a desired result.

Figure 2A:
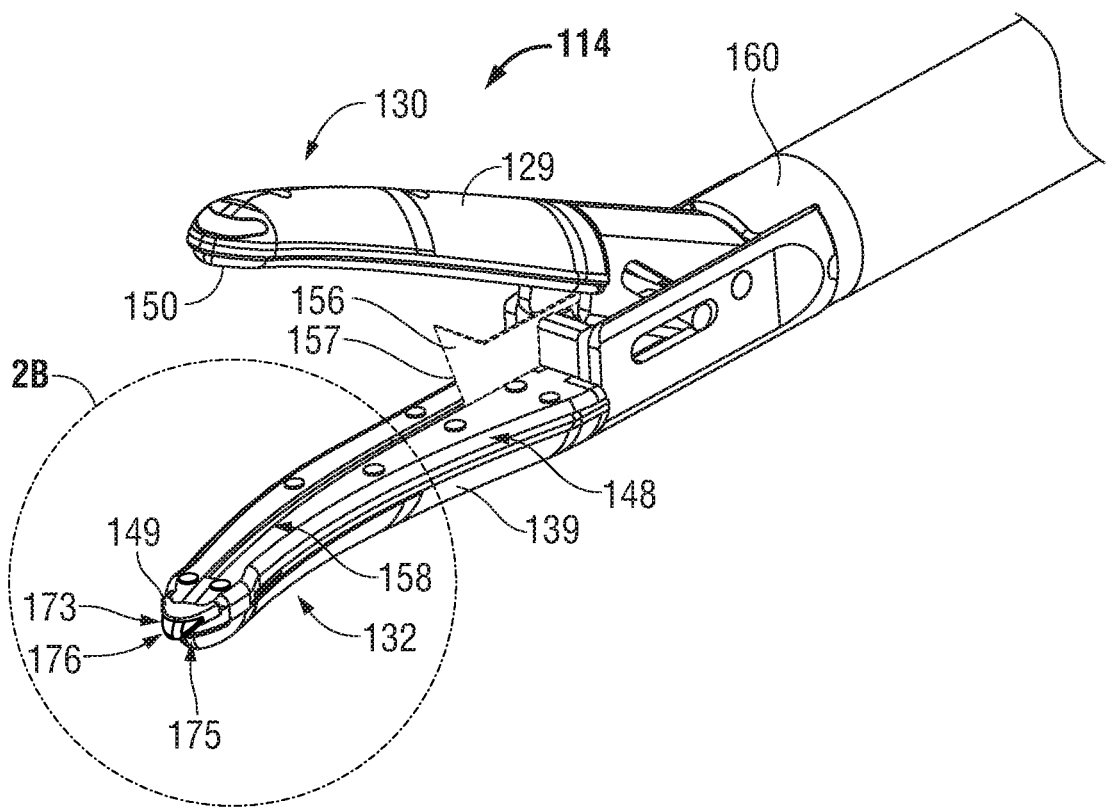
FIG. 2A is an enlarged, perspective view of the end-effector assembly of FIG. 1 depicted with a pair of opposing jaw members in an open configuration and showing a split electrode disposed in association with the lower jaw member, in accordance with an embodiment of the present disclosure.
Figure 3:
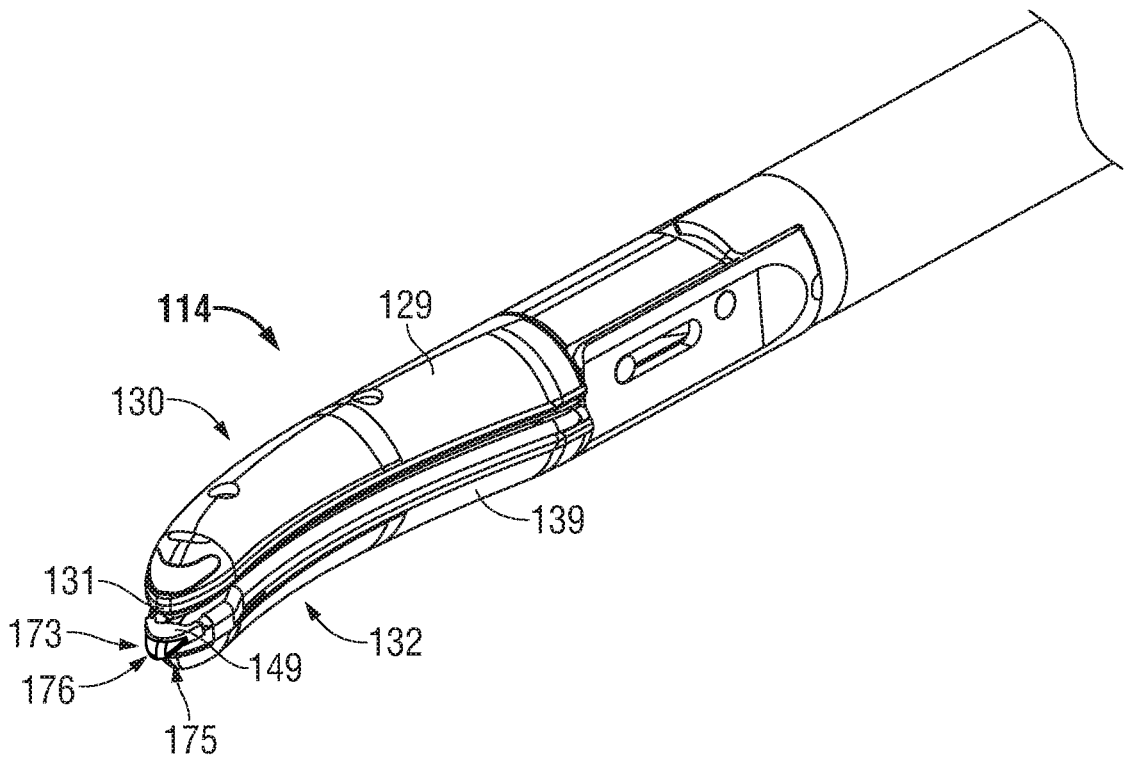
FIG. 3 is an enlarged, perspective view of the end-effector assembly of FIG. 1 showing the jaw members of FIG. 2A disposed in a closed configuration.

In some embodiments, as shown in FIGS. 1-3, the end-effector assembly 114 includes jaw members 130 and 132 in a unilateral configuration and the split electrode 176 is disposed in association with the fixed jaw member 132 (also referred to herein as the lower jaw member 132). One or more split electrodes in accordance with the present disclosure may additionally, or alternatively, be disposed in association with the moveable jaw member 130 (also referred to herein as the upper jaw member 130). In alternative embodiments, wherein opposed jaw members are arranged in a bilateral configuration, one or more split electrodes (e.g., split electrode 476 shown in FIG. 4 and/or split electrode 776 shown in FIG. 7) in accordance with the present disclosure may be disposed in association with either one or both of the jaw members.

Split electrode 176, which is described in more detail later in this description, may include any suitable electrically-conductive material, e.g., metals, metal alloys, electrically-conductive polymers, and composite materials. Split electrode 176 may be formed as a multi-layer configuration of materials.

Although FIG. 1 depicts an electrosurgical forceps 100 for use in connection with endoscopic surgical procedures, various aspects of the present disclosure may be practiced with traditional open instruments and in connection with endoluminal procedures as well. For the purposes herein, the forceps 100 is described in terms of an endoscopic instrument; however, an open version of the forceps may also include the same or similar operating components and features as described below.

Forceps 100 includes a shaft 116 having a distal end 111 configured to mechanically engage the end-effector assembly 114. The proximal end 118 of the shaft 116 is received within the housing 112, and connections relating thereto are disclosed in commonly assigned U.S. Pat. No. 7,150,097 entitled "METHOD OF MANUFACTURING JAW ASSEMBLY FOR VESSEL SEALER AND DIVIDER," commonly assigned U.S. Pat. No. 7,156,846 entitled "VESSEL SEALER AND DIVIDER FOR USE WITH SMALL TROCARS AND CANNULAS," commonly assigned U.S. Pat. No. 7,597,693 entitled "VESSEL SEALER AND DIVIDER FOR USE WITH SMALL TROCARS AND CANNULAS" and commonly assigned U.S. Pat. No. 7,771,425 entitled "VESSEL SEALER AND DIVIDER HAVING A VARIABLE JAW CLAMPING MECHANISM."

The movable handle 122 is operable to impart movement to the end-effector assembly 114 between an open configuration (FIG. 2A), wherein the opposed jaw members 130 and 132 are disposed in spaced relation relative to one another, and a clamping or closed configuration (FIG. 3), wherein the jaw members 130 and 132 are approximated. As can be appreciated, squeezing the movable handle 122 toward the stationary handle 120 serves to move the end-effector assembly 114 to the closed configuration, and separation of the movable handle 122 from the stationary handle 120 serves to move the end-effector assembly 114 to the open configuration. In some embodiments, the forceps 100 may be configured such that the trigger 126 is operable to extend and retract a knife blade 156 (FIG. 2A) through the end-effector assembly 114 when the end-effector assembly 114 is in the closed configuration.

In some embodiments, as shown in FIG. 1, forceps 100 includes an electrosurgical cable 21, which may be used to connect the forceps 100 to an electrosurgical energy source 28. Electrosurgical energy source 28 may be any generator suitable for use with electrosurgical devices, and may be configured to provide various frequencies of electromagnetic energy. Examples of electrosurgical generators that may be suitable for use as a source of electrosurgical energy are commercially available under the trademarks FORCE EZ®, FORCE FX®, FORCE TRIAD®, and LIGASURE® generator sold by Covidien Surgical Solutions of Boulder, Colo. Forceps 100 may alternatively be configured as a battery-powered wireless instrument.

FIGS. 2A through 3 show the end-effector assembly 114 of FIG. 1 in accordance with an embodiment of the present disclosure that includes a pair of electrically-conductive, tissue-engaging structures 148 and 150 (also referred to herein as tissue-engaging sealing surfaces 148 and 150, or, simply, sealing surfaces 148 and 150) disposed on the lower and upper jaw members 132 and 130, respectively. The tissue-engaging sealing surface 148 associated with the lower jaw member 132 opposes the tissue-engaging sealing surface 150 associated with the upper jaw member 130. Sealing surfaces 148 and 150 are adapted to connect to a source of electrosurgical energy for conducting electrosurgical energy through tissue grasped therebetween to effect a tissue seal.

In some embodiments, as shown in FIGS. 2A through 3, upper and lower jaw members 130 and 132 include a structural support member 129 and 139, respectively. Structural support members 129 and 139 may be formed from any suitable material or combination of materials, e.g., metal, plastic and the like. In some embodiments, the structural support members 129 and 139 may be configured to provide support for the sealing surfaces 150 and 148, respectively. Structural support members 129 and 139 may additionally, or alternatively, be configured to support an insulative substrate (not shown) or insulator thereon. The insulator, in turn, may be configured to support the sealing surfaces 150 and 148 thereon. Sealing surfaces 150 and 148 may be affixed atop the insulators and/or the structural support members 129 and 139, respectively, in any suitable manner, e.g., snap-fit, over-molding, stamping, ultrasonically welded, etc.

Figure 2B:
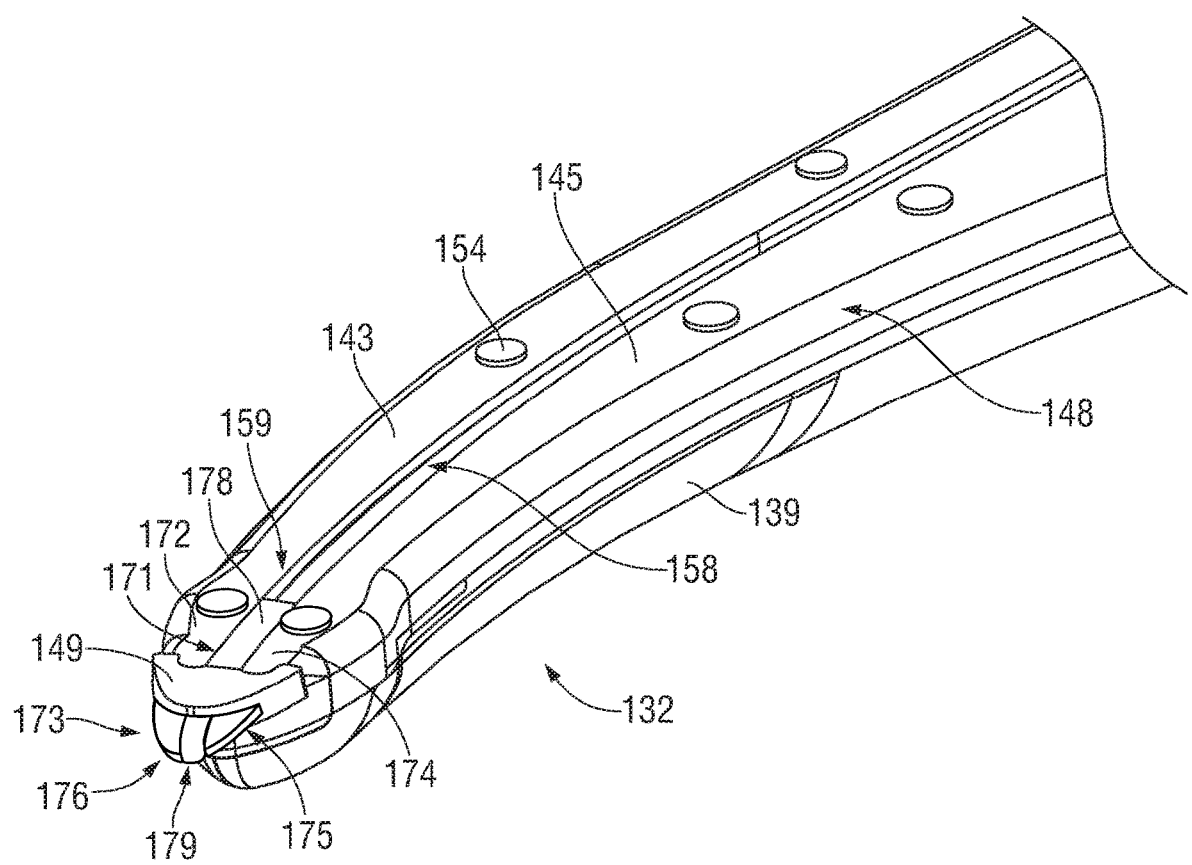
FIG. 2B is an enlarged, perspective view of the indicated area of detail of FIG. 2A.

In some embodiments, as shown in FIGS. 2A and 2B, the split electrode 176 is disposed in association with the sealing surface 148. As best seen in FIG. 2B, split electrode 176 generally includes a first electrode portion 173 defining a longitudinally-extending surface 172 and a second electrode portion 175 defining a longitudinally-extending surface 174. The longitudinally-extending surfaces 172 and 174 may have curved edges. In some embodiments, the split electrode 176, or portions thereof, is formed as a unitary component with the sealing surface 148.

End-effector assembly 114 may be moved from the open configuration (FIG. 2A), wherein tissue (not shown) is received between the jaw members 130 and 132, and the closed configuration (FIG. 3), wherein the tissue is clamped and treated. Jaw members 130 and 132 are operably coupled, e.g., pivotably mounted with respect to one another, to allow movement of the end-effector assembly 114 to the closed configuration of FIG. 3 wherein the sealing surfaces 148 and 150 provide pressure to tissue grasped therebetween. In some embodiments, when the end-effector assembly 114 is disposed in the closed configuration, a predetermined separation or gap distance is maintained between the sealing surfaces 148 and 150 by stop members (e.g., an array of stop members 154 shown in FIG. 2B) disposed on, adjacent to, or otherwise associated with, the sealing surface 148 and/or the sealing surface 150.

The lower and upper jaw members 132 and 130, respectively, are generally coupled to the electrosurgical energy source 28, e.g., through the cable 21 via respective suitable electrical wiring (not shown), to provide electrical pathways to the electrically-conductive, sealing surfaces 148 and 150 and/or the split electrode 176. The shaft 116 (FIG. 1) may include one or more suitable lumens axially disposed therethrough that serve to receive electrical wiring (not shown) configured to electrically connect the sealing surfaces 148 and 150 and/or the split electrode 176 to the electrosurgical energy source 28 through the cable 21.

As shown in FIG. 2B, the second electrode portion 175 is spaced apart from the first electrode portion 173 and electrically-isolated therefrom by a gap 171 defined therebetween. In some embodiments, as shown in FIG. 2B, the second electrode portion 175 is spaced apart from the first electrode portion 173 and electrically-isolated therefrom by an insulator 178 disposed within the gap 171. In various embodiments, the configuration of the insulator 178 can be modified so that more or less of the first electrode portion 173 and/or the second electrode portion 175 is exposed, e.g., to optimize cutting. In some embodiments, one or more portions of the surfaces 172 and 174 may include a non-electrically conductive material, e.g., electrically-insulative coating. The shape and size of the first electrode portion 173 and the second electrode portion 175 may be varied from the configuration depicted in FIGS. 2A through 3.

Insulator 178 may be formed of any suitable material providing sufficient electrical insulation to substantially prevent electrical communication between the electrically-conductive, first electrode portion 173 and the electrically-conductive, second electrode portion 175. Some examples of materials that may be suitable for forming the insulator 178 include electrically-insulative plastics such as a polyphthalamide (PPA) (e.g., Amodel®), polycarbonate (PC), acrylonitrile butadiene styrene (ABS), a blend of PC and ABS, nylon, ceramic, and silicone. In some embodiments, as shown in FIG. 2B, the insulator 178 extends from the distal end 159 of the knife channel 158 to the distal end 179 of the split electrode 176. In alternative embodiment, the distal end of the insulator 178 may be recessed from the distal end 179 of the split electrode 176, e.g., to optimize cutting.

In some embodiments, one or more portions of the split electrode 176, e.g., an inner-facing surface(s) thereof, may include an non-electrically-conductive material (or substantially non-electrically-conductive material) configured to provide electrical isolation between one or more components of the end-effector assembly 114, e.g., to reduce the chances of short circuiting the jaw members 130 and 132 and/or the sealing surfaces 148 and 150 during activation. In some embodiments, the first electrode portion 173 of the split electrode 176 may be configured to be energized with a first polarity of electrosurgical energy, and the second electrode portion 175 may be configured to be energized with a second polarity of electrosurgical energy. In some embodiments, the split electrode 176 may be configured to conduct monopolar energy to tissue. Additionally or alternatively, the split electrode 176 may be configured to electrically deactivate during sealing of tissue grasped between the tissue sealing surfaces 148 and 150.

In some embodiments, as shown in FIGS. 2A through 3, the first and second electrode portions 172 and 173, respectively, are electrically shorted together by a connector member 149. Connector member 149 may include any suitable electrically-conductive material. Connector member 149 may be coupled to the first electrode portion 172 and the second electrode portion 173 by any suitable manner of electrical connection, e.g., soldering, welding, or laser welding.

In some embodiments, the connector member 149 may be disposed distally of the distal-most end 131 of the upper jaw member 130 and/or externally to the sealing surfaces 148 and 150, e.g., to reduce the chances of short circuiting the jaw members 130 and 132 during activation, and/or to allow the gap distance to be maintained between the sealing surfaces 148 and 150.

In some embodiments, the sealing surfaces 148 and 150 are electrically coupled to opposite terminals, e.g., positive or active (+) and negative or return (−) terminals associated with the electrosurgical energy source 28. In this manner, bipolar energy may be provided through the sealing surfaces 148 and 150 to tissue. Alternatively, the sealing surfaces 148 and 150 may be configured to deliver monopolar energy to tissue. In a monopolar configuration, either one or both of the sealing surfaces 148 and 150 deliver electrosurgical energy from an active terminal, e.g., (+), while a return pad (not shown) is placed generally on the patient and provides a return path to the opposite terminal, e.g., (−), of the electrosurgical energy source 28. End-effector assembly 114 may include electrically-insulative bushings, or the like, configured to provide electrical isolation between the jaw members 132 and 130 and/or the electrically-conductive, sealing surfaces 148 and 150.

During a procedure, electrosurgical energy may be delivered to tissue through the electrically-conductive, sealing surfaces 148 and 150 to effect a tissue seal. Once a tissue seal is established, a knife blade 156 having a sharpened distal edge 157 may be advanced through a knife channel 158 defined in one or both of the jaw members 130 and 132 to transect the sealed tissue. Although the knife blade 156 is depicted in FIG. 2A as extending from the elongated shaft 116 when the end-effector assembly 114 is in an open configuration, in some embodiments, extension of the knife blade 156 into the knife channel 158 when the end-effector assembly 114 is in the open configuration is prevented.

In some embodiments, the sealing surface 148 includes a first sealing-surface portion 143 and a second sealing-surface portion 145, wherein the second sealing-surface portion 145 is separated from the first sealing-surface portion 143 by the knife channel 158. In some embodiments, wherein the sealing surface 148 includes first and second sealing-surface portions 143 and 145, respectively, the first electrode portion 173 of the split electrode 176 is electrically coupled to the first sealing-surface portion 143, and the second electrode portion 175 is electrically coupled to second sealing-surface portion 145. In some embodiments, the first and second electrode portions 173 and 175 of the split electrode 176 are formed as a unitary component with the first and second sealing-surface portions 143 and 145, respectively.

Figure 4:
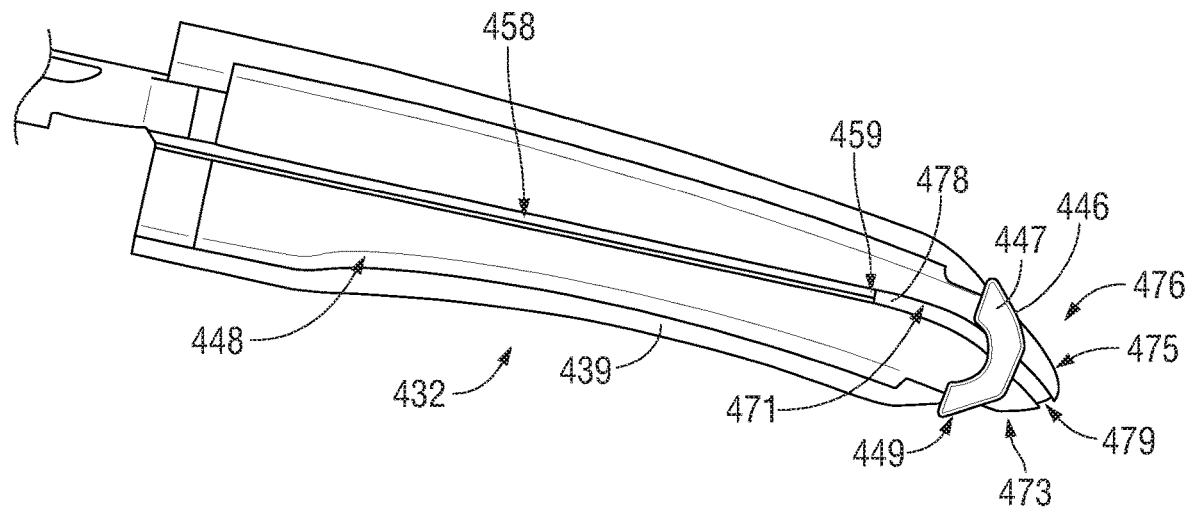
FIG. 4 is an enlarged, perspective view of a lower jaw member that includes a split electrode in accordance with an embodiment of the present disclosure.

FIG. 4 shows a split electrode 476 disposed in association with a sealing surface 448 associated with a lower jaw member 432 in accordance with the present disclosure. A portion of the split electrode 476 extends distally from a distal-most end of a lower jaw member 432. Sealing surface 448 associated with the lower jaw member 432 includes a knife channel 458. In some embodiments, as shown in FIG. 4, jaw member 432 includes a structural support member 439. Structural support member 439 may be formed from any suitable material or combination of materials, and may be configured to provide support for the sealing surface 448.

Sealing surface 448 is similar to the sealing surface 448 shown in FIG. 2A, and further description thereof is omitted in the interests of brevity.

Split electrode 476 includes a first electrode portion 473 and a second electrode portion 475. In some embodiments, the first electrode portion 473 of the split electrode 476 may be configured to be energized with a first polarity of electrosurgical energy, and the second electrode portion 475 may be configured to be energized with a second polarity of electrosurgical energy. In some embodiments, the split electrode 476 may be configured to conduct monopolar energy to tissue. Additionally or alternatively, the split electrode 476 may be configured to electrically deactivate during sealing of tissue grasped between the tissue sealing surfaces 448 and 450.

The second electrode portion 475 is spaced apart from the first electrode portion 473 and electrically-isolated therefrom by a gap 471 defined therebetween. In some embodiments, as shown in FIG. 4, the second electrode portion 475 is spaced apart from the first electrode portion 473 and electrically-isolated therefrom by an insulator 478 disposed within the gap 471. Insulator 478 extends from the distal end 459 of the knife channel 458 to the distal end 479 of the split electrode 476. In various embodiments, the configuration of the insulator 478 may be modified so that more or less of the first electrode portion 473 and/or the second electrode portion 475 is exposed to optimize cutting. Insulator 478 may be formed of any suitable material providing sufficient electrical insulation to substantially prevent electrical communication between the electrode portion 473 and the second electrode portion 475. Insulator 478 is similar to the insulator 178 shown in FIG. 2B, and further description thereof is omitted in the interests of brevity.

In some embodiments, as shown in FIG. 4, the first and second electrode portions 472 and 473, respectively, are electrically shorted together by a connector member 449. Connector member 449 includes an electrically-conductive member 446 configured to provide electrical communication between the first electrode portion 473 and the second electrode portion 475, and may include a non-electrically-conductive (or substantially non-electrically-conductive) member 447 disposed on the electrically-conductive member 446, or portion thereof. The electrically-conductive member 446 of the connector member 449 may be coupled to the first and second electrode portions 472 and 473, respectively, by any suitable manner of electrical connection, e.g., soldering, welding, or laser welding.

Figure 5:
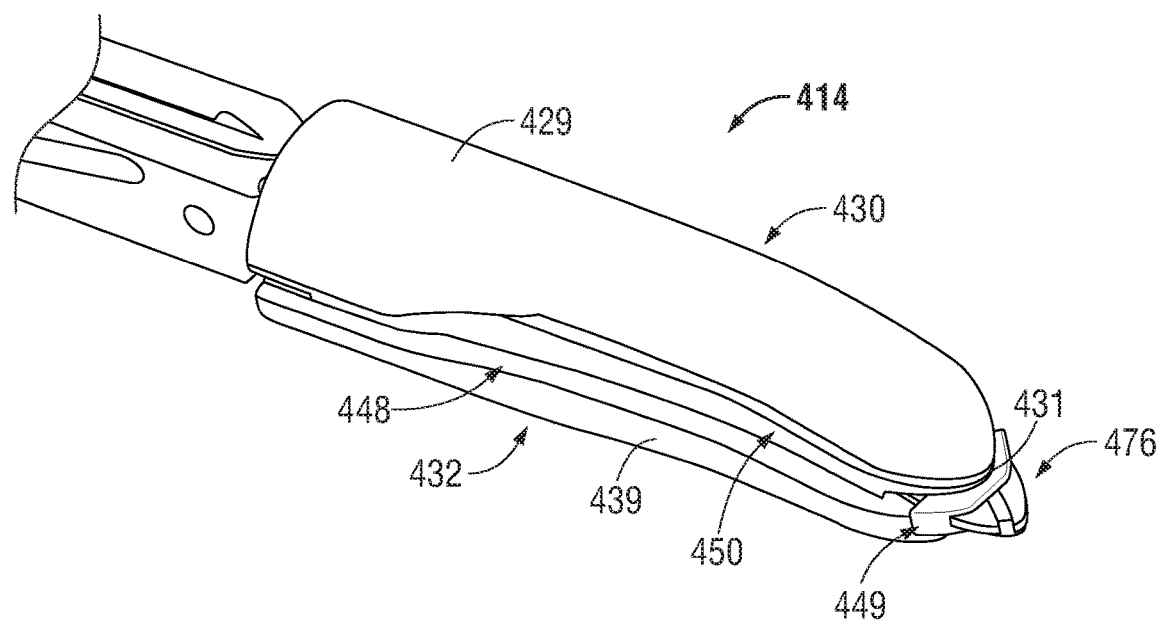
FIG. 5 is an enlarged, perspective view of an end-effector assembly that includes opposing jaw members, including the lower jaw member of FIG. 4, shown in a closed configuration in accordance with an embodiment of the present disclosure.

FIG. 5 shows an end-effector assembly 414 that includes opposing jaw members, including the lower jaw member 432 of FIG. 4 and an upper jaw member 430. At least one of the jaw members is moveable relative to the other jaw member from a first position wherein the jaw members 430 and 432 are disposed in spaced relation relative to one another to a second position wherein the jaw members 430 and 432 cooperate to grasp tissue therebetween. End-effector assembly 414 includes a sealing surface 450 associated with the upper jaw member 430. In some embodiments, as shown in FIG. 5, jaw members 430 and 432 include a structural support member 429 and 439, respectively. Structural support members 429 and 439 may be formed from any suitable material or combination of materials.

As seen in FIG. 5, at least a portion of the connector member 449 is disposed proximal to the distal-most end 431 of the upper jaw member 430. In some embodiments, when the end-effector assembly 414 is disposed in the closed configuration, a separation or gap distance is maintained between the sealing surfaces 448 and 450 by the connector member 449 either independently or in conjunction with an array of stop members (e.g., stop members 154 shown in FIG. 2B). The non-electrically-conductive member 447 of the connector member 449 may be configured to provide electrical isolation between one or more components of the end-effector assembly 414, e.g., to reduce the chances of short circuiting the jaw members 430 and 432 and/or the sealing surfaces 448 and 450 during activation.

End-effector assembly 414 may include additional, fewer, or different components than shown in FIGS. 4 and 5, depending upon a particular purpose or to achieve a desired result, and may include any feature or combination of features of the split electrode embodiments disclosed herein.

Figure 6:
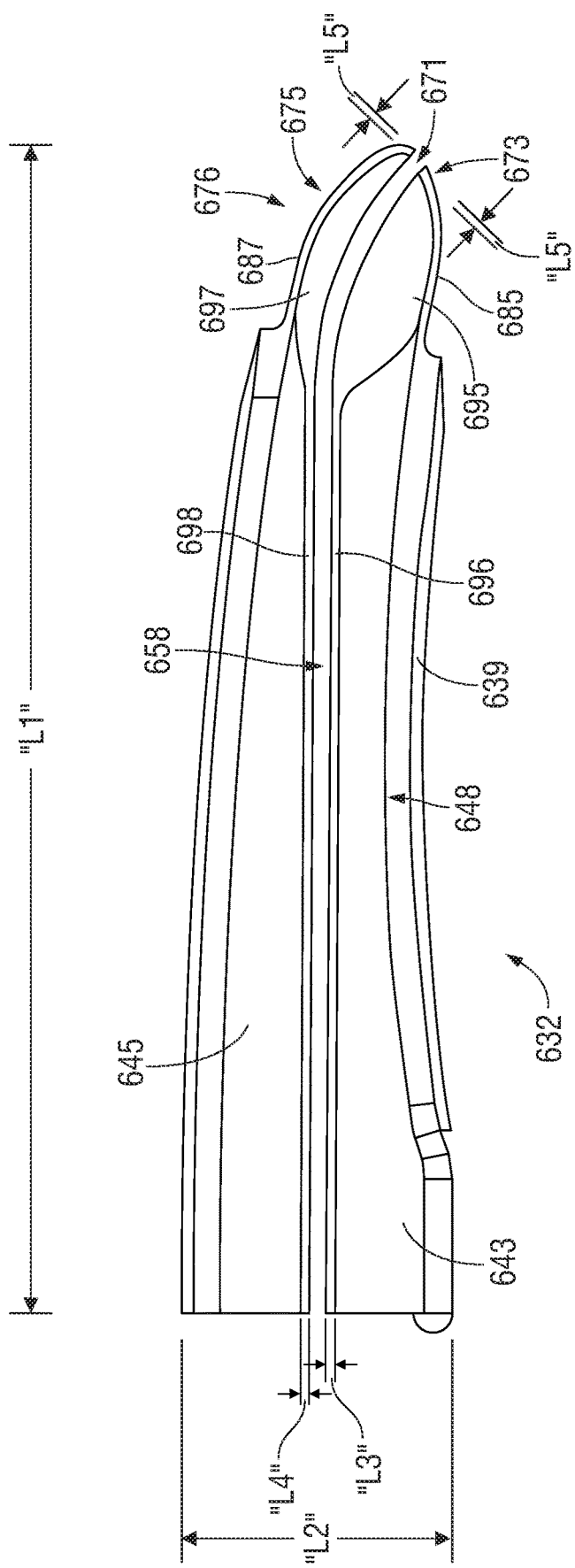
FIG. 6 is an enlarged, perspective view of a lower jaw member that includes another embodiment of a split electrode in accordance with the present disclosure.

FIG. 6 shows a split electrode 676 disposed in association with a sealing surface 648 associated with a lower jaw member 632 in accordance with the present disclosure. Jaw member 632 may have any suitable length "L1" and width "L2". In some embodiments, the length "L1" of the jaw member 632 may be about 0.700 inches, and the width "L2" of the jaw member 632 may be about 0.164 inches. Sealing surface 648 includes a longitudinally-extending knife channel 658. Sealing surface 648 includes a first sealing-surface portion 643 and a second sealing-surface portion 645, wherein the first and second sealing-surface portions 643 and 645 are spaced apart and separated from one another by the knife channel 658. In some embodiments, as shown in FIG. 6, jaw member 632 includes a structural support member 639. Structural support member 639 may be formed from any suitable material or combination of materials, and may be configured to provide support for the sealing surface 648.

Split electrode 676 includes a first electrode portion 673 and a second electrode portion 675. In some embodiments, the first electrode portion 673 of the split electrode 676 may be configured to be energized with a first polarity of electrosurgical energy, and the second electrode portion 675 may be configured to be energized with a second polarity of electrosurgical energy. In some embodiments, the split electrode 676 may be configured to conduct monopolar energy to tissue. Additionally or alternatively, the split electrode 676 may be configured to electrically deactivate during sealing of tissue grasped between the tissue sealing surfaces.

The second electrode portion 675 is spaced apart from the first electrode portion 673 and electrically-isolated therefrom by a gap 671 defined therebetween. In some embodiments, as shown in FIG. 6, the gap 671 between the first and second electrode portions 673 and 675, respectively, is disposed in communication with the knife channel 658. In some embodiments, an electrically-insulative material may be disposed within at least a portion of the gap 671, e.g., similar to the insulator 178 shown in FIG. 2B.

First electrode portion 673 includes an electrically-conductive, peripheral-edge portion 685 and a non-electrically-conductive portion 695. In some embodiments, the first electrode portion 673 and/or the electrically-conductive, peripheral-edge portion 685 thereof may be formed as a unitary component with the first sealing-surface portion 643. The non-electrically-conductive portion 695 of the first electrode portion 673 is disposed, at least in part, between the gap 671 and the electrically-conductive, peripheral-edge portion 685. The non-electrically-conductive portion 695 may include any suitable non-electrically-conductive (or substantially non-electrically-conductive) material. In some embodiments, as shown in FIG. 6, the non-electrically-conductive portion 695 of the first electrode portion 673 may include a longitudinally-extending portion 696, e.g., disposed adjacent to the knife channel 658 over the length thereof. The longitudinally-extending portion 696 may have any suitable width "L3". In some embodiments, the width "L3" of the longitudinally-extending portion 696 may be about 0.005 inches.

Second electrode portion 675 includes an electrically-conductive, peripheral-edge portion 687 and a non-electrically-conductive portion 697. The non-electrically-conductive portion 697 of the second electrode portion 675 is disposed, at least in part, between the gap 671 and the electrically-conductive, peripheral-edge portion 687, and may include any suitable non-electrically-conductive (or substantially non-electrically-conductive) material. In some embodiments, as shown in FIG. 6, the non-electrically-conductive portion 697 of the second electrode portion 675 may include a longitudinally-extending portion 698, e.g., disposed adjacent to the knife channel 658 over the length thereof. The longitudinally-extending portion 698 may have any suitable width "L4". In some embodiments, the width "L4" of the longitudinally-extending portion 698 may be about 0.005 inches.

In some embodiments, the electrically-conductive, peripheral-edge portion 685 may be configured to be energized with a first polarity of electrosurgical energy, and the electrically-conductive, peripheral-edge portion 687 may be configured to be energized with a second polarity of electrosurgical energy.

Figure 7:
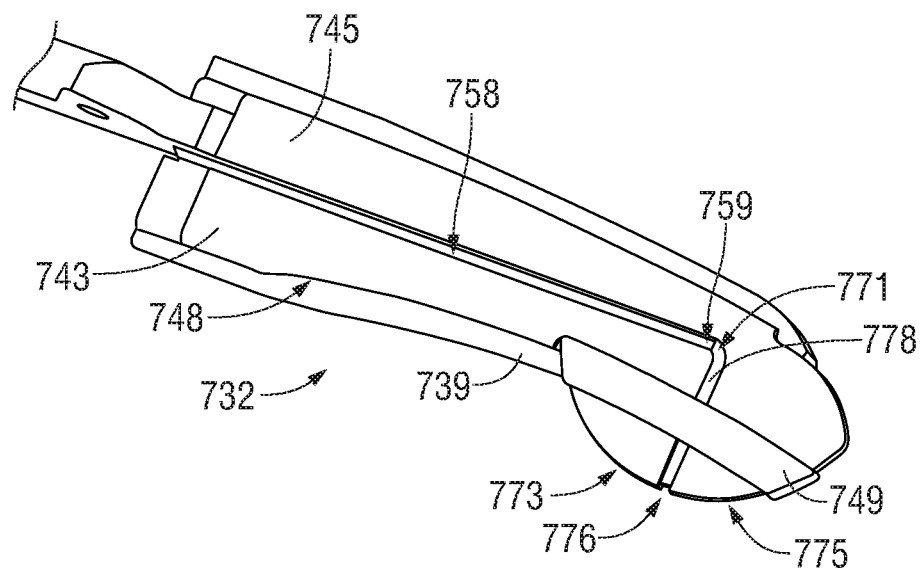
FIG. 7 is an enlarged, perspective view of a lower jaw member that includes yet another embodiment of a split electrode in accordance with the present disclosure.

FIG. 7 shows an embodiment of a split electrode 776 disposed in association with a sealing surface 748 associated with a lower jaw member 732 in accordance with the present disclosure. Sealing surface 748 includes a first sealing-surface portion 743 and a second sealing-surface portion 745, wherein the second sealing-surface portion 745 is separated from the first sealing-surface portion 743 by a longitudinally-extending knife channel 758.

Split electrode 776 includes a first electrode portion 773 and a second electrode portion 775. The first and second electrode portions 773 and 775, respectively, may be formed of any suitable electrically-conductive material, e.g., metals, metal alloys, electrically-conductive polymers, and composite materials. As described, below, with reference to FIG. 8, the shape and size of the first electrode portion 773 and/or the second electrode portion 775 may be varied from the configuration depicted in FIGS. 7 and 8.

In some embodiments, the first electrode portion 773 of the split electrode 776 may be configured to be energized with a first polarity of electrosurgical energy and the second electrode portion 775 may be configured to be energized with a second polarity of electrosurgical energy. In some embodiments, the split electrode 776 may be configured to conduct monopolar energy to tissue. Additionally or alternatively, the split electrode 776 may be configured to electrically deactivate during sealing of tissue grasped between the tissue sealing surfaces.

In some embodiments, as shown in FIG. 7, the first electrode portion 773 is disposed in association with a lateral side of the first sealing-surface portion 743, and the second electrode portion 775 is disposed in association with a distal end of the second sealing-surface portion 745. Second electrode portion 775 is spaced apart from the first electrode portion 773 and electrically-isolated therefrom by a gap 771 defined therebetween. In some embodiments, as shown in FIG. 7, the second electrode portion 775 is spaced apart from the first electrode portion 773 and electrically-isolated therefrom by an insulator 778 disposed within the gap 771.

Insulator 778 may be formed of any suitable material providing sufficient electrical insulation to substantially prevent electrical communication between the first electrode portion 773 and the second electrode portion 775. In some embodiments, the insulator 778 extends from the distal end 759 of the knife channel 758. In some embodiments, as shown in FIG. 7, the insulator 778 is axially disposed substantially perpendicular to the knife channel 758. In various embodiments, the configuration of the insulator 778 may be modified so that more or less of the first electrode portion 773 and/or the second electrode portion 775 is exposed, e.g., to optimize cutting.

Figure 8:
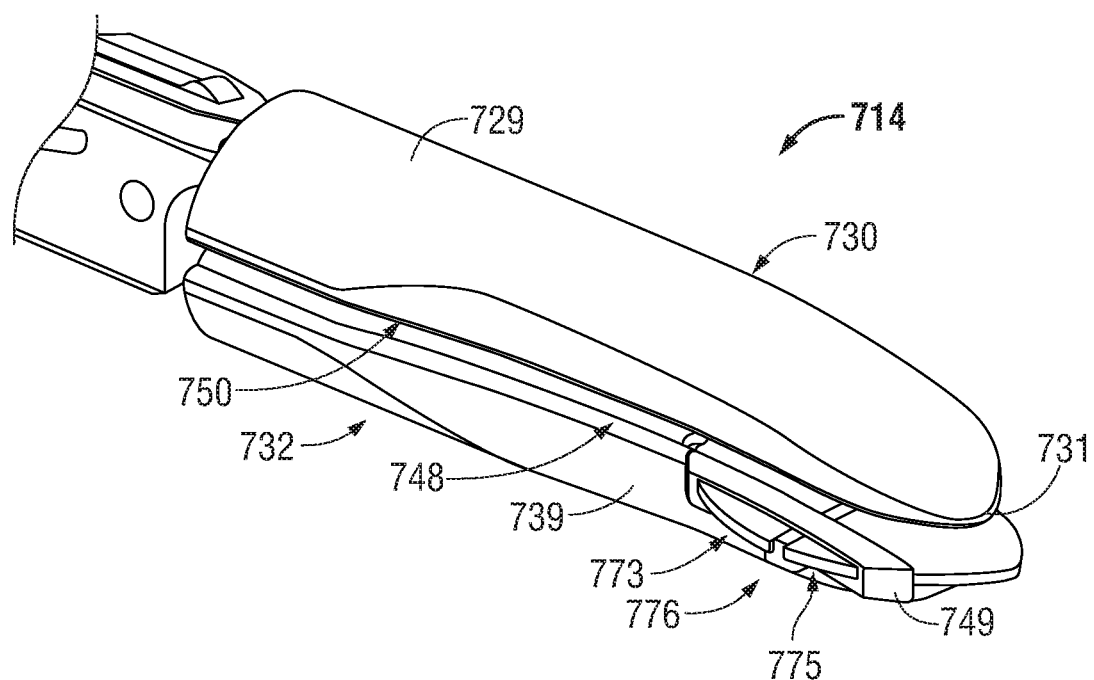
FIG. 8 is an enlarged, perspective view of an end-effector assembly that includes opposing jaw members, including the lower jaw member of FIG. 7, shown in a closed configuration in accordance with an embodiment of the present disclosure.

FIG. 8 shows an end-effector assembly 714 that includes opposing jaw members, including the lower jaw member 732 of FIG. 7 and an upper jaw member 730. At least one of the jaw members is moveable relative to the other jaw member from a first position wherein the jaw members 730 and 732 are disposed in spaced relation relative to one another to a second position wherein the jaw members 730 and 732 cooperate to grasp tissue therebetween. Sealing surfaces 748 and 750 associated with the jaw members 732 and 730, respectively, are adapted to connect to a source of electrosurgical energy (e.g., electrosurgical energy source 28 shown in FIG. 1) for conducting electrosurgical energy through tissue grasped therebetween to effect a tissue seal. In some embodiments, as shown in FIG. 8, jaw members 730 and 732 include a structural support member 729 and 739, respectively. Structural support members 729 and 739 may be formed from any suitable material or combination of materials. In some embodiments, the support members 729 and 739 may be configured to provide support for the sealing surfaces 750 and 748, respectively.

In some embodiments, as shown in FIGS. 7 and 8, a portion of the split electrode 776 extends outwardly from a lateral side of the lower jaw member 732. In some embodiments, as shown in FIG. 8, a portion of the split electrode 776 is disposed distally of the distal-most end 731 of the upper jaw member 730. In various embodiments, the configuration of the split electrode 776 may be modified so that more or less of the first electrode portion 773 and/or the laterally-extending portion of the second electrode portion 775 is exposed to optimize side cutting. Additionally or alternatively, a split electrode in accordance with the present disclosure may be associated with the sealing surface 750 associated with the upper jaw member 730.

In some embodiments, as shown in FIG. 8, the first and second electrode portions 773 and 775, respectively, are electrically shorted together by a connector member 749. Connector member 749 may include any suitable electrically-conductive material, and may be coupled to the first and second electrode portions 772 and 773, respectively, by any suitable manner of electrical connection, e.g., soldering, welding, or laser welding. As seen in FIG. 8, the connector member 749 is disposed externally to the sealing surfaces 748 and 750, e.g., to reduce the chances of short circuiting the jaw members 730 and 732 and/or the sealing surfaces 748 and 750 during activation, and/or to allow the gap distance to be maintained between the sealing surfaces.

End-effector assembly 714 may include additional, fewer, or different components than shown in FIGS. 7 and 8, depending upon a particular purpose or to achieve a desired result, and may include any feature or combination of features of the split electrode embodiments disclosed herein.

Figure 9:
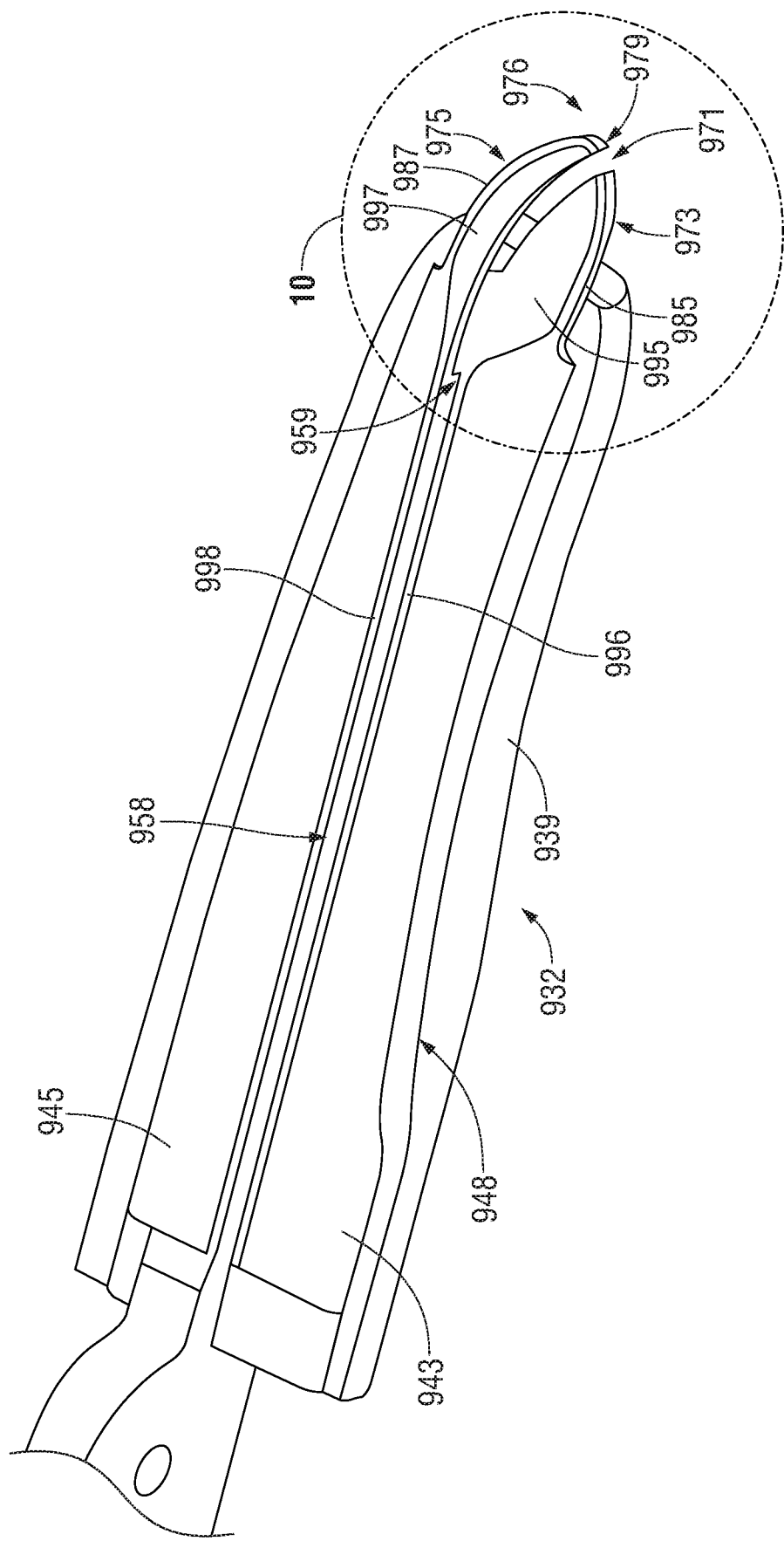
FIG. 9 is an enlarged, perspective view of a lower jaw member that includes another embodiment of a split electrode in accordance with the present disclosure.

FIG. 9 shows an embodiment of a split electrode 976 disposed in association with a sealing surface 948 associated with a lower jaw member 932 in accordance with the present disclosure. Sealing surface 948 includes a first sealing-surface portion 943 and a second sealing-surface portion 945, wherein the second sealing-surface portion 945 is separated from the first sealing-surface portion 943 by a longitudinally-extending knife channel 958. In some embodiments, as shown in FIG. 9, jaw member 932 includes a structural support member 939. Structural support member 939 may be formed from any suitable material or combination of materials, and may be configured to provide support for the sealing surface 948.

Split electrode 976 generally includes a first electrode portion 973 and a second electrode portion 975. The first and second electrode portions 973 and 975, respectively, may be formed of any suitable electrically-conductive material, e.g., metals, metal alloys, electrically-conductive polymers, and composite materials. First electrode portion 973 includes an electrically-conductive, peripheral-edge portion 985 and a non-electrically-conductive portion 995. In some embodiments, the non-electrically-conductive portion 995 of the first electrode portion 973 includes a stop bar 955. Stop bar 955, which is described in more detail with reference to FIG. 10, is generally disposed at the distal end of the knife channel 958, and may provide for enhanced device rigidity and/or proper, reliable, and consistent cutting processes.

Second electrode portion 975 includes an electrically-conductive, peripheral-edge portion 987 and a non-electrically-conductive portion 997. Second electrode portion 975 is spaced apart from the first electrode portion 973 and electrically-isolated therefrom by a gap 971 defined therebetween.

In some embodiments, the first electrode portion 973 of the split electrode 976 may be configured to be energized with a first polarity of electrosurgical energy and the second electrode portion 975 may be configured to be energized with a second polarity of electrosurgical energy. In some embodiments, the split electrode 976 may be configured to conduct monopolar energy to tissue. Additionally or alternatively, the split electrode 976 may be configured to electrically deactivate during sealing of tissue grasped between the tissue sealing surfaces.

Figure 10:
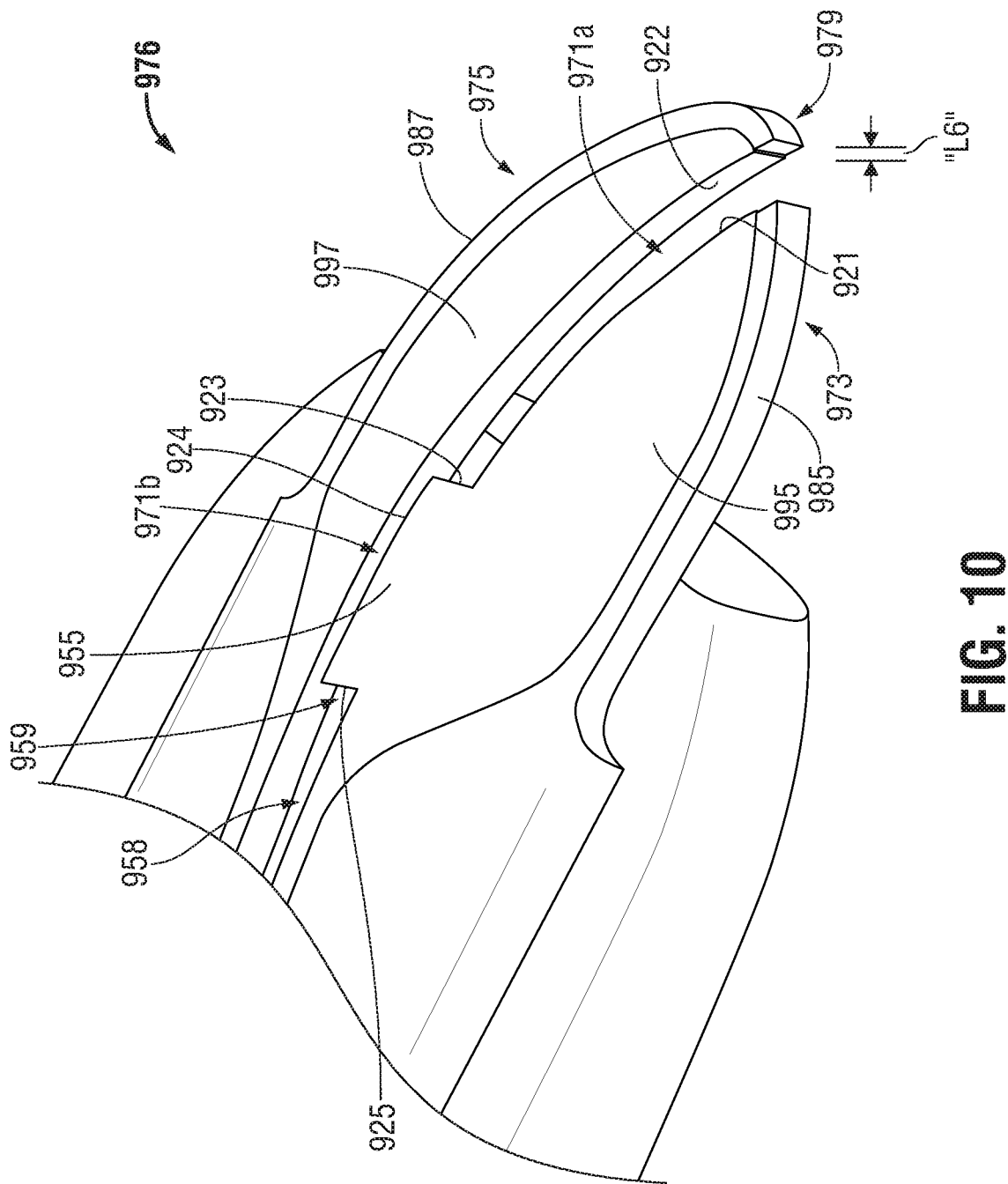
FIG. 10 is an enlarged, perspective view of the indicated area of detail of FIG. 9.

As seen in FIGS. 9 and 10, the gap 971 has a generally step-like shape defined by a first gap portion 971a and a second gap portion 971b, wherein the second gap portion 971b is disposed in communication with the first gap portion 971a and extends proximally therefrom. As best seen in FIG. 10, first electrode portion 973 includes a stop bar 955 having a proximal wall 925 disposed at or near the distal end 959 of the knife channel 958. In some embodiments, the first electrode portion 973 of the split electrode 976 is formed as a unitary component with the stop bar 955. In some embodiments, as shown in FIG. 9, the stop bar 955 is disposed within the non-electrically-conductive portion 995 of the first electrode portion 973. In alternative embodiments, the stop bar 955 may be disposed within the non-electrically-conductive portion 995 of the second electrode portion 975.

In some split-electrode gap embodiments, as shown in FIG. 10, the opposing inner walls 922 and 921 of the first and the second electrode portions 973 and 975, respectively, define the width of the first gap portion 971a, over the length defined between the distal end 979 of the split electrode 976 and the distal wall 923 of the stop bar 955. The width of the second gap portion 971b is defined between the opposing inner wall 921 and 922 of the first and second gap portion 971a and 971b, respectively, over the length defined between the distal wall 923 of the stop bar 955 and the distal end 959 of the knife channel 958.

Figure 11:
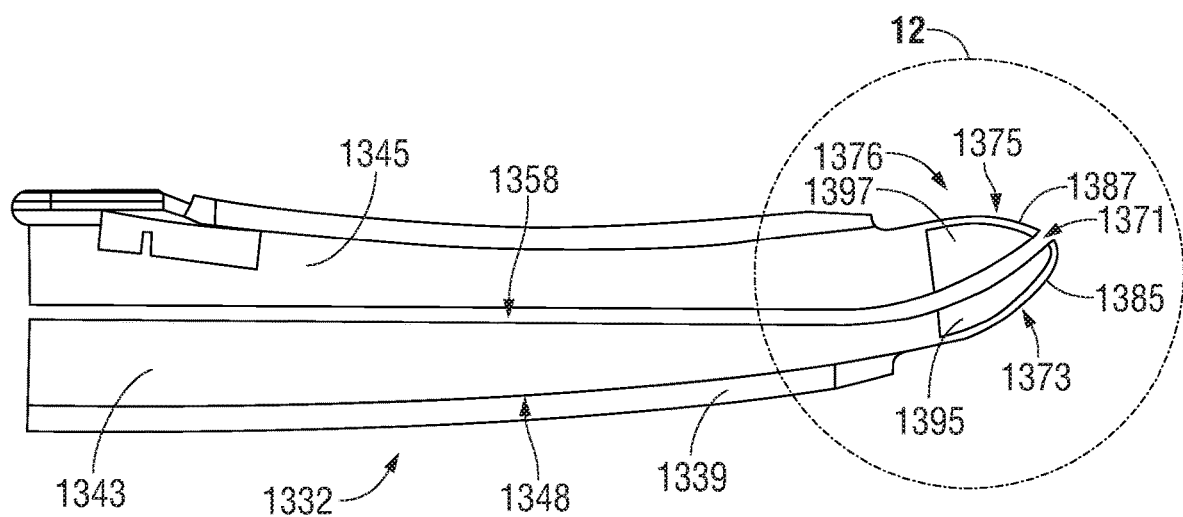
FIG. 11 is an enlarged, perspective view of a lower jaw member that includes yet another embodiment of a split electrode in accordance with the present disclosure.

Non-electrically-conductive portion 995 is disposed, at least in part, between the electrically-conductive, peripheral-edge portion 985 and the gap 971. Non-electrically-conductive portion 997 is disposed, at least in part, between the electrically-conductive peripheral-edge portion 987 and the gap 971. Non-electrically-conductive portions 995 and 997 may include any suitable non-electrically-conductive (or substantially non-electrically-conductive) material. In various embodiments, the configuration of the first gap portion 971a and/or the second gap portion 971b can be modified geometrically so that more or less of the first electrode portion 973 and the second electrode portion 975 is exposed to optimize cutting. In various embodiments, In some embodiments, when the end-effector assembly 914 is disposed in the closed configuration, a separation or gap distance is maintained between the sealing surfaces FIG. 10 is an enlarged, perspective view of the indicated area of detail of FIG. 9 in accordance with an embodiment of the present disclosure FIG. 11 shows an embodiment of a split electrode 1376 disposed in association with a sealing surface 1348 associated with a lower jaw member 1332 in accordance with the present disclosure. Sealing surface 1348 includes a first sealing-surface portion 1343 and a second sealing-surface portion 1345, wherein the second sealing-surface portion 1345 is separated from the first sealing-surface portion 1343 by a longitudinally-extending knife channel 1358. In some embodiments, as shown in FIG. 11, jaw member 1332 includes a structural support member 1339. Structural support member 1339 may be formed from any suitable material or combination of materials, and may be configured to provide support for the sealing surface 1348.

Split electrode 1376 generally includes a first electrode portion 1373 and a second electrode portion 1375. First and second electrode portions 1373 and 1375, respectively, may be formed of any suitable electrically-conductive material. First electrode portion 1373 includes an electrically-conductive, peripheral-edge portion 1385 and a non-electrically-conductive portion 1395.

Second electrode portion 1375 includes an electrically-conductive, peripheral-edge portion 1387 and a non-electrically-conductive portion 1397. Second electrode portion 1375 is spaced apart from the first electrode portion 1373 and electrically-isolated therefrom by a gap 1371 defined therebetween.

In some embodiments, the first electrode portion 1373 of the split electrode 1376 may be configured to be energized with a first polarity of electrosurgical energy and the second electrode portion 1375 may be configured to be energized with a second polarity of electrosurgical energy. In some embodiments, the split electrode 1376 may be configured to conduct monopolar energy to tissue. Additionally or alternatively, the split electrode 1376 may be electrically configured to deactivate during sealing of tissue grasped between the tissue sealing surfaces.

Figure 12:
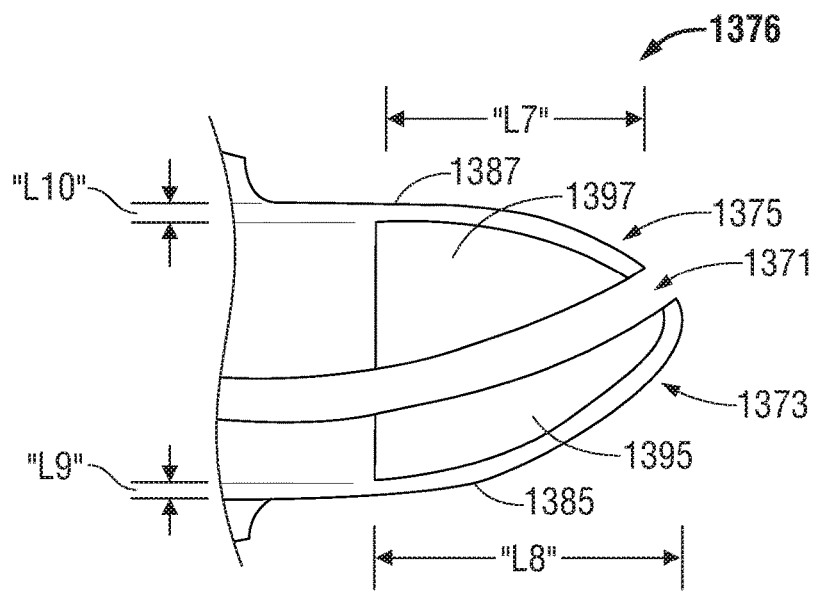
FIG. 12 is an enlarged, perspective view of the indicated area of detail of FIG. 13.

Referring to FIG. 12, the non-electrically-conductive portion 1397 of the second electrode portion 1375 (FIG. 11) may have any suitable length "L7", and the non-electrically-conductive portion 1395 of the first electrode portion 1373 (FIG. 11) may have any suitable length "L8". In some embodiments, the length "L7" of the non-electrically-conductive portion 1397 may be about 0.075 inches, and the length "L8" of the non-electrically-conductive portion 1395 may be about 0.086 inches. The electrically-conductive, peripheral-edge portion 1385 of the first electrode portion 1373 may have any suitable width "L9", and the electrically-conductive, peripheral-edge portion 1387 of the second electrode portion 1375 may have any suitable width "L10". In some embodiments, the width "L9" of the electrically-conductive, peripheral-edge portion 1385 may be about 0.005 inches. In some embodiments, the width "L10" of the electrically-conductive, peripheral-edge portion 1387 may be about 0.005 inches.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An end-effector assembly, comprising:
   a first jaw member; and
   a second jaw member coupled to the first jaw member, the first and second jaw members movable relative to one another between open and closed configurations, the first jaw member including:
   an electrically-conductive sealing surface extending along a length of the first jaw member, the electrically-conductive sealing surface adapted to connect to a source of electrosurgical energy for conducting electrosurgical energy through tissue grasped between the first and second jaw members to effect a tissue seal; and
   a split electrode operably associated with a distal end portion of the electrically-conductive sealing surface, the split electrode including:
   a first electrode portion extending from a first longitudinal section of the electrically-conductive sealing surface and having a non-electrically conductive inner portion defining a first portion of a tissue-contacting surface of the split electrode and an electrically-conductive peripheral-edge portion disposed along an outer periphery of the non-electrically conductive inner portion of the first electrode portion and defining a first outer portion of the tissue-contacting surface of the split electrode; and
   a second electrode portion extending from a second longitudinal section of the electrically-conductive sealing surface and having a second non-electrically conductive inner portion defining a second portion of the tissue-contacting surface of the split electrode and an electrically-conductive peripheral-edge portion disposed along an outer periphery of the non-electrically conductive inner portion of the second electrode portion and defining a second outer portion of the tissue-contacting surface of the split electrode, wherein the first and second electrode portions define a gap therebetween that extends along a length of the split electrode.

2. The end effector assembly according to claim 1, wherein the electrically-conductive sealing surface defines a longitudinally-extending knife channel, the knife channel contiguous with the gap of the split electrode.

3. The end effector assembly according to claim 1, wherein the non-electrically conductive inner portion of the split electrode has a stop bar protruding laterally into the gap and is monolithically formed with the non-electrically conductive inner portion.

4. The end effector assembly according to claim 3, wherein the gap has a proximal section having a first width, and a distal section having a second width greater than the first width.

5. The end effector assembly according to claim 1, wherein the non-electrically conductive inner portion of the first electrode portion is disposed between the electrically-conductive peripheral-edge portion of the first electrode and the gap and wherein the non-electrically conductive inner portion of the second electrode portion is disposed between the electrically-conductive peripheral-edge portion of the second electrode and the gap.

6. The end effector assembly according to claim 1, wherein the peripheral-edge portion is monolithically formed with the electrically-conductive sealing surface.

7. The end effector assembly according to claim 1, wherein the first jaw member further includes a structural support member having the electrically-conductive sealing surface supported thereon.

8. An electrically-conductive, tissue-engaging structure suitable for use in an electrosurgical jaw member, comprising:
- an electrically-conductive sealing surface adapted to connect to a source of electrosurgical energy for conducting electrosurgical energy therethrough; and
- a split electrode extending from a distal end portion of the electrically-conductive sealing surface, the split electrode including:
  - a first electrode portion extending from a first longitudinal section of the electrically-conductive sealing surface and having a non-electrically conductive inner portion defining a first portion of a tissue-contacting surface of the split electrode and an electrically-conductive peripheral-edge portion disposed along an outer periphery of the non-electrically conductive inner portion of the first electrode portion and defining a first outer portion of the tissue-contacting surface of the split electrode; and
  - a second electrode portion extending from a second longitudinal section of the electrically-conductive sealing surface and having a second non-electrically conductive inner portion defining a second portion of the tissue-contacting surface of the split electrode and an electrically-conductive peripheral-edge portion disposed along an outer periphery of the non-electrically conductive inner portion of the second electrode portion and defining a second outer portion of the tissue-contacting surface of the split electrode, wherein the first and second electrode portions define a gap therebetween that extends along a length of the split electrode.

9. The electrically-conductive, tissue-engaging structure according to claim 8, wherein the electrically-conductive sealing surface includes:
- a first sealing surface portion having the first electrode portion extending distally therefrom; and
- a second sealing surface portion having the second electrode portion extending distally therefrom, the second sealing surface portion spaced from the first sealing surface portion by a longitudinally-extending knife channel.

10. The electrically-conductive, tissue-engaging structure according to claim 9, wherein the knife channel is contiguous with the gap of the split electrode.

11. The electrically-conductive, tissue-engaging structure according to claim 8, wherein the non-electrically conductive inner portion of the first electrode portion has a stop bar protruding laterally into the gap.

12. The electrically-conductive, tissue-engaging structure according to claim 11, wherein the gap has a proximal section having a first width, and a distal section having a second width greater than the first width.

13. The electrically-conductive, tissue-engaging structure according to claim 8, wherein the non-electrically conductive inner portion of the first electrode portion is disposed between the peripheral-edge portion of the first electrode portion and the gap.

14. The electrically-conductive, tissue-engaging structure according to claim 9, wherein the peripheral-edge portion of the first electrode portion is monolithically formed with the first sealing surface portion, and the peripheral-edge portion of the second electrode portion is monolithically formed with the second sealing surface portion.

* * * * *